US00PP27587P3

(12) United States Plant Patent
Jelenkovic et al.

(10) Patent No.: US PP27,587 P3
(45) Date of Patent: Jan. 24, 2017

(54) STRAWBERRY PLANT NAMED 'NJ99-204-1'

(50) Latin Name: *Fragaria ananassa*
Varietal Denomination: NJ99-204-1

(71) Applicant: Rutgers, The State University, New Brunswick, NJ (US)

(72) Inventors: Gojko J. Jelenkovic, Piscataway, NJ (US); Laurie P. Lutz, Rockville, MD (US); Peter J. Nitzsche, Long Valley, NJ (US); William T. Hlubik, Bordentown, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 12 days.

(21) Appl. No.: 13/999,932

(22) Filed: Apr. 4, 2014

(65) Prior Publication Data

US 2015/0289431 P1 Oct. 8, 2015

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Susan McCormick Ewoldt
(74) *Attorney, Agent, or Firm* — James A. Lucas; Driggs, Hogg, Daugherty & Del Zoppo Co., LPA

(57) ABSTRACT

A new and distinct cultivar of strawberry plant (*Fragaria× ananassa*), was developed from seed produced by a hand pollinated cross between 'NJ96-12-1' and 'Camarosa' (U.S. Plant Pat. No. 8,708). The new strawberry named 'NJ99-204-1' is distinguished by its ability to produce large, smooth, long wedge and conical shaped fruit, with attractive red color and excellent flavor. 'NJ99-204-1' plants have vigorous growth and an upright form.

3 Drawing Sheets

Latin name of genus and species of the plant claimed: *Fragaria ananassa.*

Variety denomination: STRAWBERRY PLANT NAMED 'NJ99-204-1'.

CROSS REFERENCE TO RELATED APPLICATIONS

NONE

STATEMENT REGARDING FEDERALLY SPONSORED RESEARCH OR DEVELOPMENT

NONE

BACKGROUND OF THE NEW PLANT

A new and distinct cultivar of strawberry (*Fragaria× ananassa*) named 'NJ99-204-1' is a short day, June bearing cultivar similar to 'Chandler' (U.S. Plant Pat. No. 5,262), but it is distinguished by its large fruit with long wedge to long conical shape, uniform deep red color, and exceptional flavor. The cultivar is well adapted to high density plasticulture growing systems and has been shown to perform well in the eastern United States (Zones 5b, 6a & b, 7a & b, 8a & b). 'NJ99-204-1' should be of commercial value, particularly for farmers with pick-your-own operations or access to local farmers markets. In this fresh market segment, the excellent shape, color and flavor of 'NJ99-204-1' fruit will appeal to consumers who are increasingly interested in locally produced flavorful fruit.

ORIGIN OF THE VARIETY

'NJ99-204-1' was developed in the controlled strawberry breeding program at a major New Jersey University. The female parent was 'NJ96-12-1', an unpatented variety from the program. 'NJ96-12-1' was chosen for its flavorful fruit with high eating quality even though 'NJ96-12-1' plants were small with moderate yield and medium sized fruit. The male parent was 'Camarosa', a commercial strawberry variety (U.S. Plant Pat. No. 8,708). 'Camarosa' is not known for outstanding flavor, but it was chosen to bolster plant and fruit size in the offspring of the cross, as it is known for vigorous plant growth and large firm fruit. A 'Camarosa' male parent was also used in the co-pending application of 'NJ00-48-3' (U.S. Ser. No. 13/999,928).

Seeds of the 'NJ96-12-1' and 'Camarosa' cross were germinated in a greenhouse and planted in the field at a research farm located in New Brunswick, N.J. in 1999. The selected seedling designated as 'NJ99-204-1' was recognized for its vigor, healthy phenotype, productivity and superior fruit quality. The 'NJ99-204-1' plant was then asexually propagated using stolons. 'NJ99-204-1' was found to reproduce true to type through successive generations of asexual reproduction. 'NJ99-204-1' was evaluated in observational and replicated trials in several locations in New Jersey and one location in North Carolina from 2000 to 2016 .

BRIEF DESCRIPTION OF THE PHOTOGRAPHS

DETAILED BOTANICAL DESCRIPTION

The following botanical description of the 'NJ99-204-1' plant is based on spring observations on mature plants at experimental farms in North Brunswick and Pittstown, N.J. Plants were produced from rooted stolons that were planted in the field the previous fall. Plants were grown following common plasticulture practices for the eastern United States.

All color references below are measured against The Royal Horticultural Society Colour Chart (R.H.S. 5$^{th}$ Ed. 2007). Colors of leaves, flowers and fruit may vary with the age of the plant part, and year to year variations in abiotic and biotic conditions.

Figure 2:
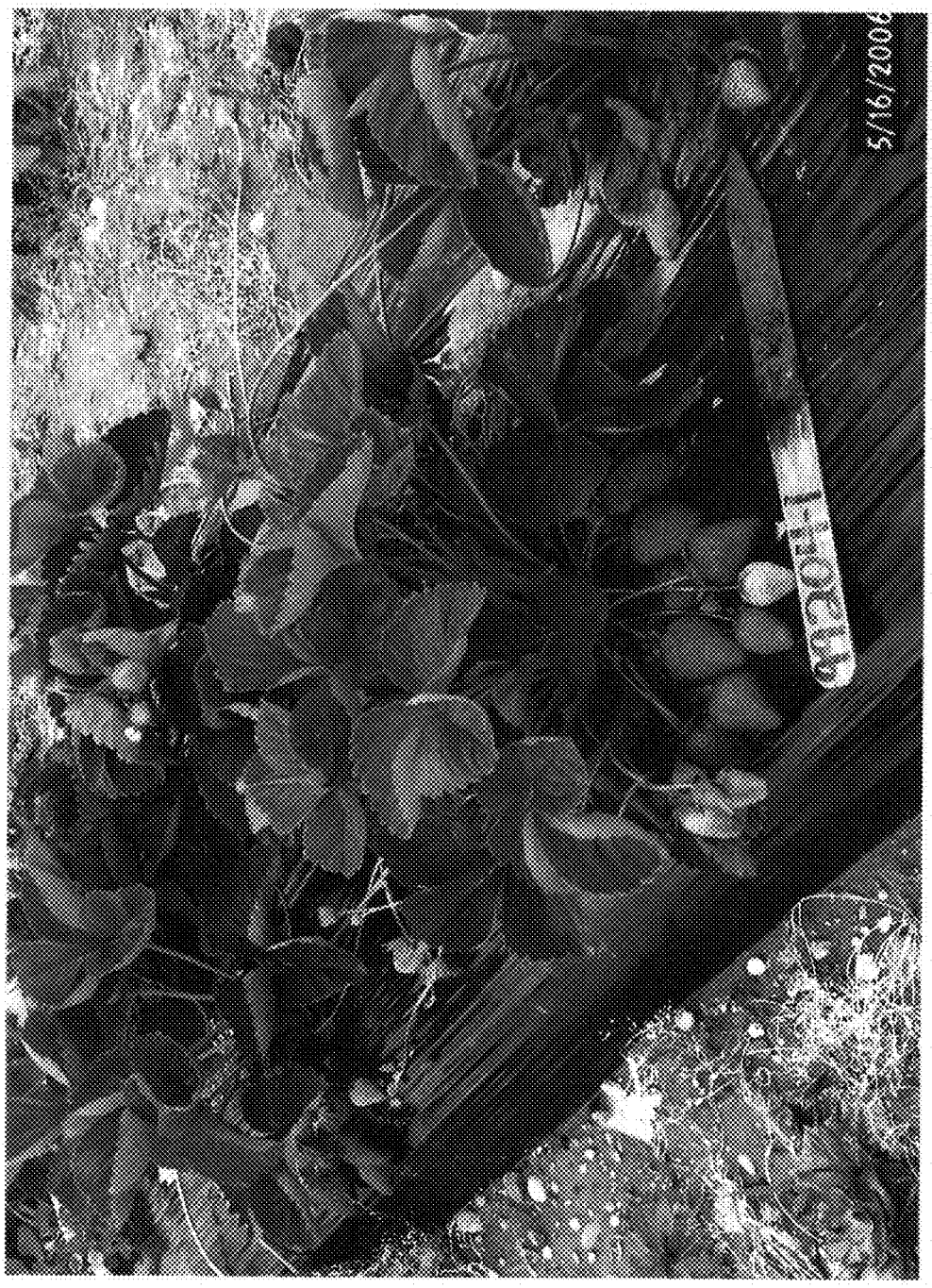
FIG. 2 illustrates plant and fruit characteristics after the fruit has matured on the 'NJ99-204-1' plant.

'NJ99-204-1' leaf petioles show upright directional growth rather than prostrate, resulting in an upright plant growth habit (FIG. 2). In the plasticulture system used in Pittstown, N.J., with plants grown 30 cm apart in double staggered rows, average 'NJ99-204-1' plant diameter (not including stolons) was 47 cm and average plant height was 29 cm. 'NJ99-204-1' plant vigor was medium. 'NJ99-204-1' plants developed 4 crowns per plant and 4 stolons per crown on average (Pittstown, N.J., 2016).

'NJ99-204-1' leaf width is 16 to 23 cm. The lobes of the trifoliate leaves are of medium size, oblong in shape, leathery in structure with a presence of numerous hairs on both the upper and lower surfaces. The upper leaf surface color is green (RHS 137A-B) and the lower leaf surface is yellow-green (RHS 147B). 'NJ99-204-1' leaf petiole length is 15 to 27 cm, petiole diameter is 0.5 cm, and petiole color is yellow-green (RHS 146D). 'NJ99-204-1' leaf petioles have abundant, mostly outwards hair. This distinguishes 'NJ99-204-1' from 'Chandler' which has smooth petioles with no or sparse hair. 'NJ99-204-1' stipules at the base of the petiole are 2.7 cm long and 0.8 cm wide on average. The stipule surface is smooth and light green with medium anthocyanin coloration (RHS N34C-35C).

Terminal leaflets have an obtuse shape of base and serrate to crenate margins with 23 serrations on average. Terminal leaflet length and width of blades are 9.9 and 8.9 cm on average, respectively. The terminal leaflet petiolule is 1.1 cm long on average, etiolule diameter averages 0.2 cm, and petiolule color is green (RHS 146D). The petiolule has abundant, mostly outwards hair.

Figure 1:
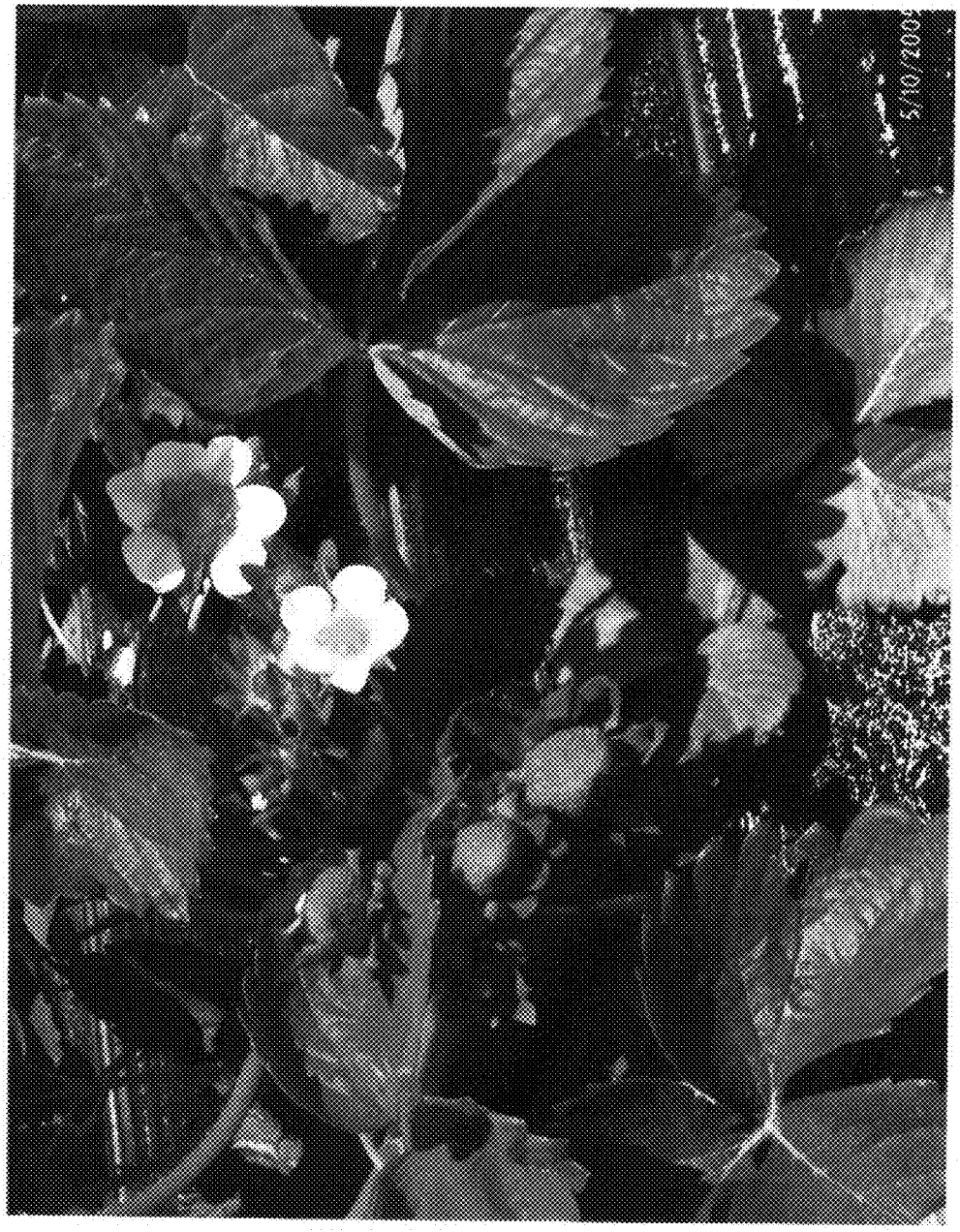
FIG. 1 illustrates the initial stages of typical flowers and fruit developing on a 'NJ99-204-1' plant.

The position of the 'NJ99-204-1' inflorescence is level with the foliage. 'NJ99-204-1' plants developed 33 to 77 flowers with an average of 54 flowers per plant. Plants were in full flower early to mid-May (Pittstown, N.J., 2016). 'NJ99-204-1' flower petals are white (RHS155B) and are as long as wide (FIG. 1, TABLE 1). Petals have a rounded shape on the outside of the flower and a convergent shape at the base of the flower. Flowers have 5 petals and 11 sepals on average. The average diameter of the corolla is larger than that of the calyx (TABLE 1). The attitude of the pedicel hair is upwards. The hermaphroditic flowers have numerous pistils and −24 plump anthers loaded with well-developed functional pollen grains. Observations in different years and locations indicate that the pollination process is regular, leading to formation of well-shaped, attractive fruits.

Two types of 'NJ99-204-1' fruit truss structures are found. Fruit trusses that developed in early spring may have few pedicels of equal diameter, and similarly sized fruit. Branching of the peduncle occurred early in its development, before emerging from the bud, and the peduncle is not visible. However, in the most common type of 'NJ99-204-1' fruit truss there is a clearly visible peduncle (0.4 to 0.5 cm in diameter, RHS 146D), a central thick pedicel with the largest, primary, fruit and thinner secondary and tertiary pedicels with successively smaller fruit. The most common fruit truss measured 21 cm from the base till the primary fruit on average. In comparison, 'Chandler' fruit trusses are usually longer with an average of 25 cm. For both varieties, the weight of the fruit brings down the trusses and in plasticulture fruit usually lies on the plastic that covers the raised bed.

Figure 3:
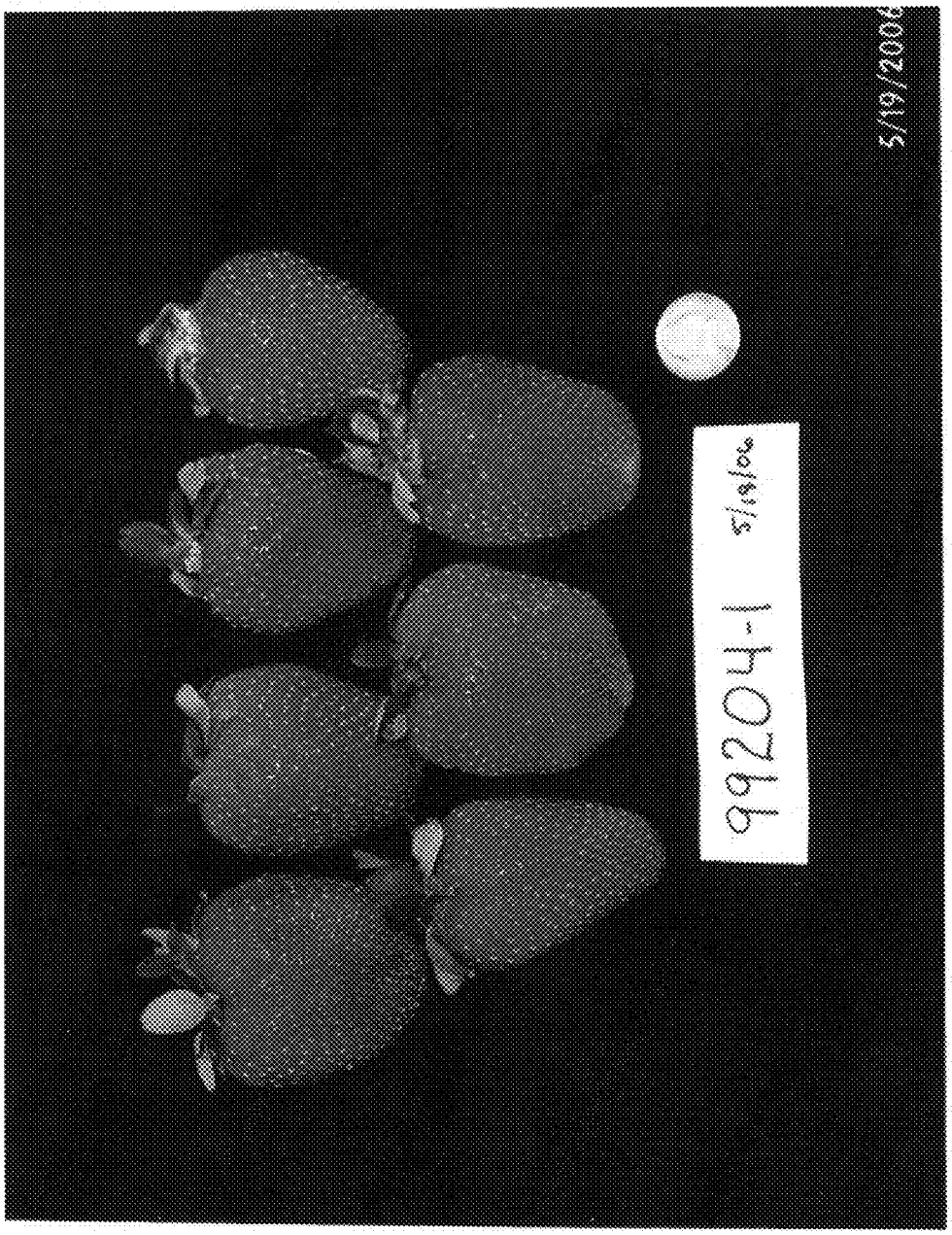
FIG. 3 illustrates the characteristics (shape, size and coloring) of typical ripened fruit from a 'NJ99-204-1' plant.

'NJ99-204-1' primary fruit is usually wedge shaped with uplifted sepals and conspicuous fruit neck. Primary fruit is notably longer than wide with an average 1.3 (Pittstown, N.J., 2015) to 1.4 (Pittstown, N.J., 2016, TABLE 2) length to width ratio. 'NJ99-204-1' secondary fruit is predominantly conic in shape. Secondary fruit is only slightly longer than wide with a 1.1 length to width ratio. In comparison, the difference in length/width ratio between 'Chandler' primary and secondary fruit was less pronounced. 'NJ99-204-1' fruit has a regular, smooth surface with dark red color (RHS 45A-53A) (FIG. 3). Fruit flesh and core are red (RHS 46A and 46C, respectively). The fruit cavity is absent or small. The position of the achenes is level with the fruit surface. Achenes are yellow-green (RHS 152C-D). The number of achenes per fruit counted on 5 secondary fruit averaged 230.

From the time of flowering to the time of fruit ripening (harvesting) it normally takes about 28-34 days; which categorizes this genotype as a mid-season (June bearing) variety. Fruit turns red acropetally, from the top of the fruit toward the tip. Under particularly warm conditions in the spring, a primary fruit can become completely red in a single day. However, formation of sugars, aromatics and other quality constituents that give 'NJ99-204-1' fruit its unique flavor requires at least two additional days.

MARKET USE OF THE VARIETY

'NJ99-204-1' resulted from a cross of 'Camarosa' with a selection that had flavorful fruit but low production. In the co-pending application of 'NJ00-48-3', 'Camarosa' was crossed with 'Earliglow' (unpatented) which is known for its sweet fruit.

'NJ99-204-1' fruit is darker red than that of 'NJ00-48-3', and 'NJ99-204-1' achenes are level with the fruit surface, as opposed to below the fruit surface for 'NJ00-48-3'. 'NJ99-204-1' primary fruit has a larger length/width ratio than that of secondary fruit. This difference was not observed for 'NJ00-48-3'. Fruit from 'NJ99-204-1' and 'NJ00-48-3' each has its own distinctive flavor.

Both 'NJ99-204-1' and 'NJ00-48-3' have the potential to produce large fruit and commercially viable marketable yield in the eastern United States (TABLES 3 AND 4). These new varieties are alternatives for 'Chandler' which is currently the standard variety grown in plasticulture systems in the eastern United States.

SUMMARY OF THE VARIETY

'NJ99-204-1' is primarily adapted to the climate and conditions of the eastern United States where it demonstrates vigorous plant growth. 'NJ99-204-1' is characterized by its production of large, smooth, long wedge and conical shaped fruit, with attractive red color and

TABLE 1

Flower characteristics of 'NJ99-204-1', NJ00-48-3' and 'Chandler', Pittstown, New Jersey 2016

| Characteristic[x] | 'NJ99-204-1' | 'NJ00-48-3' | 'Chandler' |
|---|---|---|---|
| Corolla diameter | 37 | 33 | 33 |
| Calyx diameter | 30 | 28 | 27 |

TABLE 1-continued

Flower characteristics of 'NJ99-204-1', NJ00-48-3' and 'Chandler', Pittstown, New Jersey 2016

| Characteristic[x] | 'NJ99-204-1' | 'NJ00-48-3' | 'Chandler' |
|---|---|---|---|
| Petal length | 14 | 13 | 13 |
| Petal width | 14 | 15 | 15 |
| Petal color | White (155B) | White (155B) | White (155B) |
| Inner Sepal length | 10 | 11 | 10 |
| Outer Sepal length | 10 | 8 | 7 |
| Inner Sepal width | 7 | 6 | 5 |
| Outer Sepal width | 6 | 5 | 5 |
| Sepal color | Green (141A) | Green (141A) | Green (141A) |

[x]Data are averages of 10 observations on secondary flowers. Petals and sepals were spread out flat for corolla and calyx diameter measurements. All length and width measurements are in millimeters. Color references are measured against The Royal Horticultural Society Colour Chart (R.H.S. 5th Ed. 2007).

TABLE 2

Fruit characteristics of 'NJ99-204-1', 'NJ00-48-3' and 'Chandler', Pittstown, New Jersey 2016

| Characteristic[x] | 'NJ99-204-1' | 'NJ00-48-3' | 'Chandler' |
|---|---|---|---|
| Primary Fruit Length (mm) | 50 | 40 | 40 |
| Primary Fruit Width (mm) | 37 | 36 | 35 |
| Primary Fruit Thickness (mm) | 34 | 32 | 32 |
| Primary Fruit Length/Width | 1.4 | 1.1 | 1.2 |
| Primary Fruit Weight (g) | 26 | 20 | 20 |
| Secondary Fruit Length (mm) | 40 | 37 | 36 |
| Secondary Fruit Width (mm) | 36 | 34 | 34 |
| Secondary Fruit Thickness (mm) | 33 | 31 | 31 |
| Secondary Fruit Length/Width | 1.1 | 1.1 | 1.1 |
| Secondary Fruit Weight (g) | 21 | 17 | 17 |

[x]Data are averages of 20 measurements.

TABLE 3

Field performance of strawberry selections and cultivars, Salisbury, NC, 2010

| | 'NJ99-204-1' | 'Chandler' | 'Camarosa' | 'Florida Radiance'* | 'Galletta'** |
|---|---|---|---|---|---|
| Marketable yield (lb/A) | 22,756 | 28,352 | 19,363 | 14,816 | 12,775 |
| Average fruit size (g)[y] | 23.5 | 21.9 | 24.1 | 23.0 | 26.1 |
| % Soluble Solids (Brix)[z] | 8.00 | 7.16 | 7.67 | 5.98 | 7.75 |

[y]Average of twenty five representative fruit/plot

[z]Average of samples from Apr. 29, May 3, and May 5, 2010

*U.S. Plant Pat. No. 20,363

**U.S. Plant Pat. No. 19,763

TABLE 4

Field performance of 'NJ99-204-1', 'NJ00-48-3', 'Camarosa' and 'Chandler', Pittstown and North Brunswick, NJ, 2013-2016

| Trial Location and Harvest Year | 'NJ99-204-1' | 'NJ00-48-3' | 'Camarosa' | 'Chandler' |
|---|---|---|---|---|
| | Marketable Yield[x] (lb/A) | Marketable Yield[x] (lb/A) | Marketable Yield[x] (lb/A) | Marketable Yield[x] (lb/A) |
| Pittstown 2013 | 15,937 | | | 12,420 |
| Pittstown 2014 | 7,193 | | 8,392 | 9,018 |
| Pittstown 2015 | 16,407 | 18,412 | | 16,938 |
| Pittstown 2016 | 15,785 | 11,392 | | 16,456 |
| North Brunswick 2013 | 7,484 | 5,635 | | 4,191 |
| North Brunswick 2014 | 8,432 | 11,216 | 14,371 | 12,187 |
| North Brunswick 2015 | 14,347 | 17,643 | | 16,193 |
| | Fruit Weight[x,y] (g) | Fruit Weight[x,y] (g) | Fruit Weight[x,y] (g) | Fruit Weight[x,y] (g) |
| Pittstown 2013 | 20.9 | | | 18.5 |
| Pittstown 2014 | 19.7 | | 21.9 | 19.2 |
| Pittstown 2015 | 15.6 | 16.3 | | 15.1 |
| Pittstown 2016 | 20.5 | 18.9 | | 17.6 |
| North Brunswick 2013 | 13.2 | 13.8 | | 12.0 |
| North Brunswick 2014 | 18.6 | 18.1 | 18.8 | 17.1 |
| North Brunswick 2015 | 17.1 | 17.5 | | 17.9 |
| | Brix[z] (%) | Brix[z] (%) | Brix[z] (%) | Brix[z] (%) |
| Pittstown 2013 | 7.6 | | | 7.1 |
| Pittstown 2014 | 9.0 | | 7.6 | 7.9 |
| Pittstown 2015 | 7.8 | 7.0 | | 7.0 |
| Pittstown 2016 | 9.2 | 9.0 | | 8.5 |
| North Brunswick 2013 | 8.5 | 8.9 | | 8.3 |
| North Brunswick 2014 | 8.8 | 8.3 | 7.6 | 8.3 |
| North Brunswick 2015 | 8.2 | 7.8 | | 7.7 |

'NJ00-48-3' and 'Camarosa' present in part of the trials

[x]Averages of 4 plots, except 'Chandler' 3 plots for Pittstown 2013

[y]Weighted average fruit weight. Total marketable yield per plot was divided by total number of fruit harvested per plot. Total number of fruit harvested per plot was estimated by dividing marketable yield by average fruit weight for each harvest (determined on a sample of 20 fruit, or on all fruit if fewer than 20 present), and summing the number of fruit for all harvests.

[z]Average of % Brix determined at 2 to 5 harvests

We claim:

1. A new and distinct strawberry plant named 'NJ99-204-1' as herein illustrated and described.

* * * * *